(12) United States Patent
Tsoukalis

(10) Patent No.: US 9,468,715 B2
(45) Date of Patent: Oct. 18, 2016

(54) INFUSION ROTARY PERISTALTIC PUMP

(71) Applicant: Seagate Technology LLC, Cupertino, CA (US)

(72) Inventor: Achilleas Tsoukalis, Gerakas (GR)

(73) Assignee: MICREL MEDICAL DEVICES S.A., Gerakas (GR)

(*) Notice: Subject to any disclaimer, the term of this patent is extended or adjusted under 35 U.S.C. 154(b) by 202 days.

(21) Appl. No.: 14/029,030

(22) Filed: Sep. 17, 2013

(65) Prior Publication Data
US 2014/0081202 A1   Mar. 20, 2014

(30) Foreign Application Priority Data

Sep. 17, 2012  (GR) ................................. 120100467
Jun. 26, 2013  (EP) .................................... 13173745

(51) Int. Cl.
*A61M 5/142*   (2006.01)
*A61M 5/48*    (2006.01)
*A61M 5/36*    (2006.01)
*F04B 43/12*   (2006.01)

(52) U.S. Cl.
CPC .......... *A61M 5/142* (2013.01); *A61M 5/14232* (2013.01); *A61M 5/36* (2013.01); *A61M 5/484* (2013.01); *F04B 43/1253* (2013.01)

(58) Field of Classification Search
CPC ...... A61M 5/36; A61M 5/142; A61M 5/145; A61M 5/155; A61M 5/484; A61M 5/14232; F04B 43/12; F04B 43/1253
USPC ........................ 604/67, 123, 131, 153, 408; 417/477.1–477.14
See application file for complete search history.

(56) References Cited

U.S. PATENT DOCUMENTS

| | | | |
|---|---|---|---|
| 249,285 A | 11/1881 | Allen | |
| 2,412,397 A | 12/1946 | Harper | |
| 5,342,181 A | 8/1994 | Schock et al. | |
| 5,655,897 A | 8/1997 | Neftel et al. | |
| 5,980,490 A | 11/1999 | Tsoukalis | |
| 6,165,154 A | 12/2000 | Gray et al. | |
| 6,202,708 B1 | 3/2001 | Bynum | |
| 6,494,694 B2 | 12/2002 | Lawless et al. | |
| 6,572,349 B2 | 6/2003 | Sorensen et al. | |
| 6,626,792 B2 | 9/2003 | Vranish | |
| 6,685,450 B2 | 2/2004 | Bandis et al. | |

(Continued)

OTHER PUBLICATIONS

U.S. Appl. No. 13/864,927, filed Oct. 17, 2013, Tsoukalis.

*Primary Examiner* — Edelmira Bosques
*Assistant Examiner* — Leah Swanson
(74) *Attorney, Agent, or Firm* — Hollingsworth Davis, LLC

(57) ABSTRACT

An infusion pump comprises at least three operating layers. A first layer includes epicyclic gear means comprising a rotatable central gear, a stationary outer ring gear, and movable planet gears arranged between the central gear and the ring gear in movable engagement with the central and ring gears. A second layer includes roller bearing means comprising a stationary outer ring and a movable inner roller arrangement in movable arrangement with the outer ring and coupled with the epicyclic gear means to provide a rotational bearing for the central and planet gears. A third layer includes rotary peristaltic pump means comprising stationary flexible tubing which includes a bent portion having an essentially part-cycle form and a rotor having engagement elements to squeeze the bent portion during rotation for a pump action, wherein the rotor is coupled with the central gear to transfer torque from the central gear to the rotor.

25 Claims, 11 Drawing Sheets

(56) References Cited

U.S. PATENT DOCUMENTS

| | | |
|---|---|---|
| 7,074,021 B2 | 7/2006 | Byrne |
| 7,918,657 B2 | 4/2011 | Bobo et al. |
| 8,062,009 B2 | 11/2011 | Cueni |
| 2003/0040700 A1* | 2/2003 | Hickle et al. .................. 604/67 |
| 2008/0095645 A1 | 4/2008 | Tam |
| 2009/0074597 A1* | 3/2009 | Martin et al. ............. 417/477.1 |
| 2012/0016295 A1 | 1/2012 | Tsoukalis |
| 2012/0040797 A1 | 2/2012 | Fox |
| 2012/0289895 A1 | 11/2012 | Tsoukalis |

\* cited by examiner

INFUSION ROTARY PERISTALTIC PUMP

BACKGROUND OF THE INVENTION

The present invention relates to an infusion pump device.

In medical practice, infusion pumps have been used in various ways to pump and forward liquid pharmaceutical substances, wherein the oldest method using a rotary peristaltic pump has been set up in 1881 which pump comprises an elastic pipe fixed in the edges of a "U", a rotating spool, peripheral rotors in the rounded portion of the "U", and a tightened rubber used to close the free flow and to pump the enclosed liquid to an exit nozzle (cf. U. S. Pat. No. 249,285 A). The deficiency of this arrangement, that the pipe is pulled in upstream direction and is amassed in the downstream direction which destroys the accuracy of the dose, was historically corrected by U.S. Pat. No. 2,412,397 A in 1943 which teaches the provision of a linear peristaltic pump and has been therefore called "linear peristaltic" and is currently greatly preferred in the majority of the medical infusion pumps using three or more fingers to gradually squeeze a resilient tube against a plate for forwarding the liquid. For such an arrangement, U.S. Pat. No. 5,980,490 A discloses the provision of six finger followers driven by respective cams for squeezing a linear resilient pipe so as to close it gradually and push the liquid without any pulling of the pipe since the followers are moved only vertically and therefore no longitudinal force occurs.

By adding a spool pressure cylinder in the perimeter where the resilient tubing is pressed against it, the accuracy of the rotary peristaltic pump could be improved because it was not necessary anymore to pull the tubing for closing the flow anymore, but the tubing continues to be tightened by the peristaltic motion of passive rollers. Recently, the rotary peristaltic pump is provided with a flexible, but inelastic sheet inserted between the rotors of the spool and the pipe so that the pipe is not pulled due to the rotation, or similarly with inelastic liner-fibers inserted inside the resilient tubing in order to avoid pulling. Furthermore, the rotor has been provided with active (and not passive) rotating rollers (having gears) so that the pipe is not pulled, and more recently the tubing is fixed at the pressure cylinder (cf. U.S. Pat. Nos. 5,342,181 A and 8,062,009 A), or in a vertical arrangement the pipe is horizontally pressed against a semi-circle element (cf. U.S. Pat. No. 7,074,021 A) or against a half hard plastic element and a half elastic horizontal element (U.S. Pat. No. 6,572,349 A). U.S. Pat. No. 7,918,657 A deals with the bouncing back of the tubing after the compression for a better accuracy. A gear bearing is described in U.S. Pat. No. 6,626,792 A.

The provision of a cartridge for a medicine bag is another improvement in the prior art, which cartridge initially has had only an elastic infusion pipe (cf. U.S. Pat. No. 6,202,708 A) or more facilities such as valves (cf. U.S. Pat. No. 6,165,154 A) and/or a pressure sensor (cf. U.S. Pat. No. 6,572,349 A). Also hydraulic arrangements at the cartridge facilitate its placement onto the pump which usually requires a persistent loading procedure of the pipe and security accessories or connections in the prior art (cf. U.S. Pat. No. 6,494,694 A).

Due to the pressure on prices in the market, there is a need for developing new, more effective and cheap medical infusion pumps with better accuracy.

In the prior art, consumable pump sets contain many parts to be welded in series, such as filters, flows clamps, anti-syphon valves, and Y-connections for other tubings, i.e. many parts which are to be placed in series with an intermediary infusion tubing and many junctions of parts which must be handmade since an automatic production is too difficult, resulting in high parts costs and complicated assembly.

It is an object of the present invention to provide a consumable set having a small size appropriate for evermore smaller pumps and having all its relevant functionalities realized on one part which is to be automatically assembled.

The size, weight and portability of a pump depend on its power consumption. When the tubing is to be pressed, a high energy consumption is needed to fold its sidewall from an "O" figure gradually to an "8" figure and then to an "I" figure where the flow stops. The vertical parts of the "O" cross-section of the tubing are essentially not made to be folded, and in the linear or rotary peristaltic pumps of the prior art an unnecessary consumption of energy occurs because of the resilient tubing section form.

It is a further object of the present invention to provide an infusion pump with a small size (pocket size) for personal infusion care, usually to be provided on the body of a chronic patient, for medicines like insulin for diabetes patients, DUODOPA or Apomorphine for Parkinson patients, Flolan for pulmonary hypertension, or Immuno-globulin for immune system problems, with great accuracy and flow linearity, with easy placement of a consumable infusion cartridge by the patients themselves at home, at low costs, also with the possibility of an alternative version to be used in hospitals with a minimal-sized pump on a spike itself, with higher infusion rates for general infusions, and with the use of a user interface display which, if needed, can be linked wirelessly or wired with the pump.

The provision of multi-layer flexible plastic foils for the manufacturing of medicine bags with layers which protect the transfer of gas or vapor from and to the medicine allows the compounding of bags ready to use in the pump either as a laboratory compounding for shorter stability or as a pharmaceutical packaging for longer stability of more or less than one year.

It is a further object of the present invention to provide a consumable infusion cartridge for a pump which allows the provision of a compounding long before its use, with no risk by the user himself, while the design and construction of the device shall contain all the necessary parts mentioned above in one and the same fitting so as to minimize the manual manufacturing and bonding and to allow an automatic assembly resulting in a reduction of the costs.

SUMMARY OF THE INVENTION

The present invention proposes an improved infusion pump for pharmaceutical liquids, to be used independently or along with the device according to the applicant's co-pending patent applications US 2012/0016295 A and U.S. Ser. No. 13/864,927.

The pump according to the present invention uses a consumable infusion set which includes the largest part of an infusion mechanism and all the accessories needed for a safe infusion in various embodiments depending on the type of infusion and is provided in one cartridge which may be assembled in an auto-matic indexing machine so as to minimize costs.

The so-called parts of the cartridge preferably on the upstream side include a sealable hole for filling the bag (if any), a valve to block the compounded medicine from entering the infusion pump mechanism prior to use, which valve opens automatically by placing the pump into or onto the cartridge and furthermore can operate in a filling-in position for enabling the drug to be filled into the bag and in a sterilization-infusion position wherein the bag or upstream tubing is connected to the peristaltic mechanism, and an infusion mechanism as described below, and on the downstream side include a filter comprising a hydrophilic film being also an anti-microbial filter of several mesh sizes, wherein a hydrophobic film for avoiding the output of air is bonded over one or two ventilation holes provided in a cover, and an input of additional pharmaceutical substance (which is usually input from a Y part) with a back flow check valve.

The cartridge is coupled to a bag (if any) or a spike on the inlet side (upstream) and may be accommodated into a cassette or may be connected with an external bag through a spike or directly in case of a pre-mounted mechanism on the bag. The cartridge is coupled at the downstream side preferably to a long extension set which in the edge has a Luer connection embodied depending on the use, i.e. a male embodiment for most users, a female embodiment for enteral nutrition, specially manufactured for IV or epidural applications, wherein the tubing may have different colors for various positions of infusion like intravenous, epidural, enteral, etc.

The cartridge may also have a special code for communication with the pump by providing contacts or an optic or magnetic interface or RFID/NFC so that the pump is able to recognize the type of cartridge and the infusion route to limit the infusion protocols and to inform the user of the infusion route for safety reasons, and also the drug volume, the drug name, concentration, diluter, lot number.

According to the present invention, there is provided an infusion mechanism which may be contained on the cartridge and uses the epicyclic principle, i.e. (1) an epicyclic gear head having a central or sun gear and epicyclic rotating planet gears with a gear ratio between the central and planet gears which determines their respective rotational speed, (2) a cylindrical roller bearing wherein the rotation of the epicyclic planet cylinders is determined by the ratio between their diameters and the diameter of the central roller, and (3) a rotary peristaltic pump means where there are respective epicyclic cylindrical compression rollers squeezing a flexible, preferably resilient, pipe or tubing in a peripheral casing or housing which is also called a "drum". For realizing the aforementioned mechanism, the present invention correspondingly provides three operating stages or layers which are arranged one over the other in a single body and include an epicyclic gear layer, a roller bearing layer and an infusion layer comprising a rotary peristaltic pump means. Each operating layer may have more than one sub-stage or floor in each application for multi-pump arrangements.

According to the present invention, each layer has a discrete functional role in the device. The present invention uses the aforementioned three epicyclic similarities to make possible their use in a single three-functions-arrangement which define a planet roller/gear arrangement including a central or sun gear/roller, a planet gear/roller and an annulus system defining an external peristaltic tubing and pressure drum/bearing annulus/gear annulus. This arrangement according to the present invention requires only a minimum power consumption since there is no substantial friction of pressure rollers to a central driving rotor and there is no use of a driving carrier as in the prior art which otherwise would induce friction. Due to a high accuracy of the angular position of the rollers resulting from the operation of the epicyclic gear head, the infusion is absolutely predictable and accurate. Further, the intrinsically active smooth rolling of the rollers on and along the resilient tubing prevents the tubing from deforming and pulling.

The gear layer with preferably only two planet gears regulates in absolute accuracy the angular position of the rollers with regard to the rotation of the central roller driven by a motor, wherein the planet gears are located between the central gear and the peripheral gear (annulus) and engaged therewith as known in the prior art.

In the roller bearing layer, a pumping force onto the resilient tubing due to pressure against the drum is compensated and eliminated creating a radial reaction force from the opposite bearing ring due to a serial chain reaction transfer of the three cylinders in contact on the same rotating plane, so that there is no friction on the central driving axis. This result in a dramatic decrease of power consumption while at the same time the very important nominal distance between the gears is maintained which also contributes to the decrease of the friction and power consumption, which is otherwise not possible without a carrier.

The pumping layer preferably includes only two pressure rollers and a central driving cylinder, wherein the resilient tubing is accommodated within a cavity of the drum having preferably a "П"-shaped cross section, so that the roller-tubing compression contact line when squeezing the tubing (major compression) would be spaced by a proper radial distance so as to achieve the desired nominal downstream pressure. Such line is not necessarily at the same radial distance from the center of the bearings, but it has been found that the radial distance may be shorter for one type of tubing and larger for another type of tubing so that in the pump layer the roller is provided with a smaller diameter (insert) in the first case or with a larger diameter (excess) in the second case. Such a solution minimizes the occurrence of friction from the roller onto the tubing.

US 2008/0095645 A1 discloses a pump comprising epicyclic roller bearing and gear arrangement wherein the gears are mounted under the rollers. However, this prior art teaches neither the provision of an annulus gear nor the provision of a bearing ring, but the provision of a carrier for maintaining the required distance between the gears.

BRIEF DESCRIPTION OF THE DRAWINGS

Preferred embodiments of the present invention will now be described with reference to the drawings, in which:

FIG. 4a shows a vertical cross-section of the mechanism along line A-A of FIG. 4;

FIG. 4b shows a vertical cross-section of the mechanism along line B-B of FIG. 4;

FIG. 17 shows the spike cassette of FIG. 14 with the spike cassette infusion pump of FIGS. 15 and 16 mounted thereon;

DETAILED DESCRIPTION OF THE PREFERRED EMBODIMENTS

Figure 22:
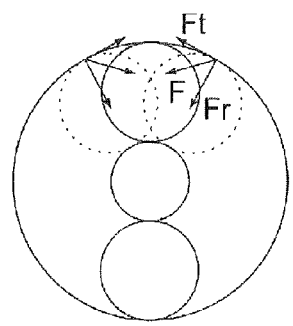
FIG. 22 is a schematic graph showing roller alignment forces when slightly misaligned in the bearing layer.

In more detail, the preferred embodiment of the rotary peristaltic mechanism 60 has preferably two snap-fitting lower and upper parts 14, 15 of a housing in which all other mechanism parts are included wherein the lower and upper parts 14, 15 define lower and upper covers of the housing and therefore commonly form the housing itself. Three cylindrical rollers 1, 2, 1 each having a gear 100, 200 at its bottom, are provided as combined driving and pumping elements, and include two planet rollers 1 of same diameter and one central roller 2, wherein all the cylindrical rollers 1, 2 are arranged in the same (rotating) plane with their rotational axis being parallel to each other and the gear/diameter ratio between the central gear 200 at the bottom of the central roller 2 and to the planet gears 100 at the bottom of the planet rollers 1 determines the reduction ratio of the rotation of the planet rollers 1 over the rotation of the central roller 2. Preferably there is no carrier to move them, which otherwise would result in additional friction, since an alignment is assured by cylindrical portions of the rollers 1, 2 located at a lower entropy point of a bearing circle, as it becomes clear in particular from the FIGS. 6 and 8 in conjunction with FIG. 4a, so that they cannot leave out of the aforementioned plane. The reason why three rollers 1, 2, 1 are always in line irrespective of their height is that the planet rollers 1 are subject to a counterforce from an outer bearing ring 16 towards their aligned position, as shown in FIG. 22 where the force F is separated into a radial component Fr and a tangential component Ft, even if the upper part of the planet roller 1 tends to slightly move out of the plane, whereas its lower part cannot move off line because of the engagement of the gears 100, 200.

Figure 6:
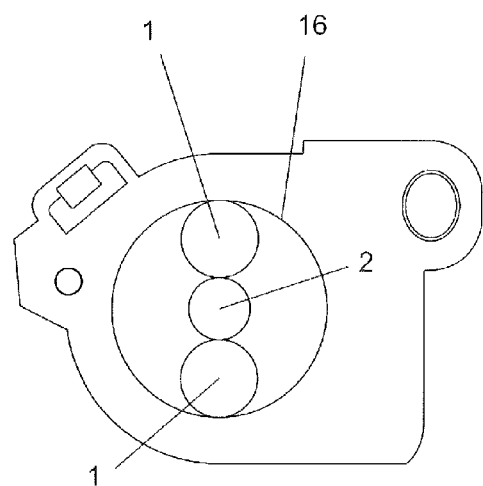
FIG. 6 shows a horizontal cross-section of the mechanism in a bottom bearing layer.
Figure 7:
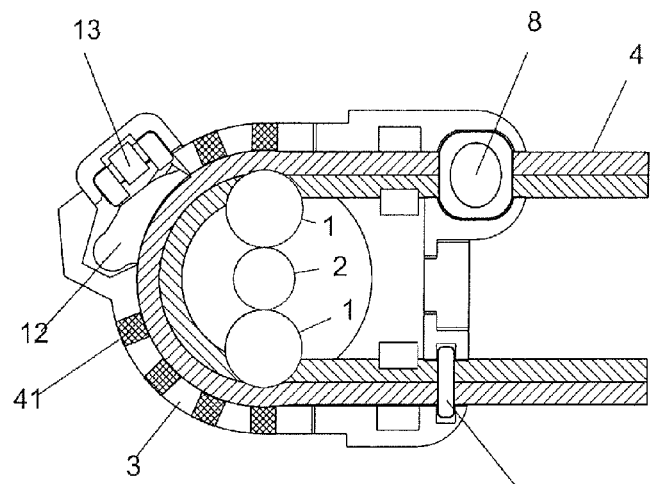
FIG. 7 shows a horizontal cross-section of the mechanism in a peristaltic pump layer.
Figure 8:
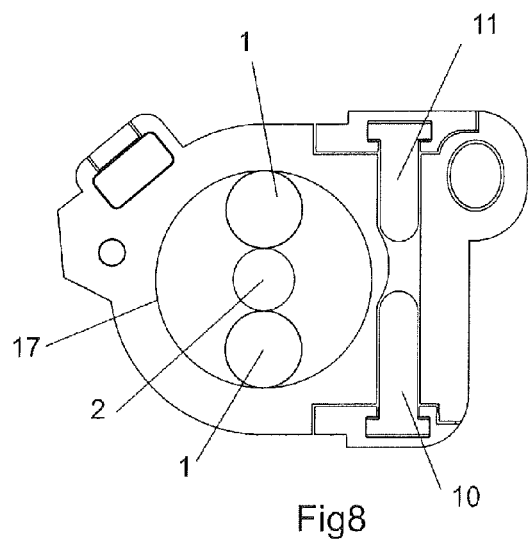
FIG. 8 shows a horizontal cross-section in an upper bearing layer.

The rollers 1 roll inside along two cylindrical bearing rings 16, 17 each forming a bearing layer or stage as shown in FIGS. 6 and 8. The rollers 1 further extend through a pumping layer or stage for rolling along a resilient tubing 4 and squeezing it which tubing is arranged in the pumping layer and accommodated in a cavity of a casing 3 having a "Π"-shaped cross section, as shown in particular in the FIGS. 3, 4b and 7. At the bottom and, hence, in the lower part 14 of the mechanism 60 there is a gear layer or stage comprising an outer annulus gear 7, two planet gears 100 and a central gear 200 which commonly form an epicyclic gear per se known in the art, wherein the central gear 200 creates a rotating moment onto the planet gears 100 against the outer gear 7. The two planet rollers 1 and the central roller 2 are all three in contact with each other and roll on each other so that the resilient tubing 4 included in the aforementioned cavity is squeezed by the planet rollers 1, as schematically shown in FIGS. 4a and 4b and 7. When doing so, radial forces are compensated and, hence, eliminated by the bearing in the two roller bearing layers or stages so that a pin-like central axis 210, 220, 230 which coaxially extend through the central roller 2 is not subject to any radial friction in a bushing 300 each formed in the lower part 14 and the upper part 15, wherein the upper and lower ends 210, 220 of the central axis extend through the bushings 300. Rather, the bushings 300 simply hold the central axis to maintain the alignment of the three rollers 1, 2 and to beware them of a side dislocation.

The tangential component of the forces results in a rotating moment and, hence, a torque around the central gear 200 (which is also called a sun gear), equal to the torque in the central roller 2 which is driven by a motor (not shown). Such torque makes the rollers 1, 2 rotate for a peristaltic infusion, without the occurrence of any friction achieved by a powered carrier as found in prior art peristaltic mechanisms.

The present invention may provide a safe infusion pump with only two squeezing rollers 1, which results in an advantage of having more infusion by 50% per rotation and a lower tubing compression power reduced by 30% in contrast to prior art pumps having three rollers (achieving a 120° infusion cyclus) resulting in a corresponding saving of energy.

In the prior art, there exist solutions to eliminate radial forces and frictions by the use of ball bearings within the rotation axis of the carrier (cf. US 2012/0040797 A1). However, there is no reference to use epicyclic gears only for the accurate rotation and transfer of a rolling torque without a power transmitting carrier. Preferably, the rollers 1, 2, 1 and the outer ring 16, 17 of the bearing layer are made of hard bearing low friction plastic like Acetal for reduction of the rolling friction to a minimum.

Infusion cartridges or cassettes which contain a rotary peristaltic mechanism 60 with a central drive axis and epicyclic rollers which, however, do not provide a bearing in the meaning of the present invention are known in the prior art, but with uncertain accuracy of infusion due to occurrence of friction at all (cf. U.S. Pat. No. 5,655,897 A) or due to occurrence of friction in the carrier which is effective to maintain the nominal distance between the gear rollers (cf. U.S. Pat. No. 6,685,450 A and US 2008/0095645 A1).

According to the drawings, a preferred embodiment of the rotary peristaltic mechanism 60 according to the present invention comprises (a) a 360° annulus body including the outer gear 7 of the epicyclic gear and two outer rings 16, 17 of the roller bearings, (b) the resilient tubing 4 fixed with hooks 41 on the casing 3 for major infusion accuracy because of both radial and tangential movement immobilization for approximately 180° in the rotary peristaltic pump, (c) preferably only two planet rollers 1 for a higher infusion volume per rotation and a lower compression power, and (d) a central cylindrical axis 210, 220, 230 which is not connected with the planet rollers 1 by any other means except for the engagement between the central roller 2 and the planet rollers 1 in the bearing layers and between the central gear 200 and the planet gears 100 in the gear layer.

The geometry of the path is sufficient for correcting the angular positioning of the rollers 1, 2 and their parallelism for each rotation angle of the central axis 210, 220, 230, the transfer of relative torque and its conversion into the squeezing of the tubing 4.

The mechanism 60 has three operating layers or stages over its height. A preferred implementation as shown has a first operating layer with epicyclic gears 7, 100, 200, a second layer which defines a roller bearing layer including a first roller bearing 1, 2, 16, a third layer which is a pumping layer including a rotary peristaltic pump means 1, 2, 4, and finally on top a fourth layer which defines a second roller bearing layer including a second roller bearing 1, 2, 17. Due to this arrangement, a proper distribution of forces in the bearings are achieved, wherein the cavity of the casing 3 accommodating the tubing 4 forms a "Π" with its height being limited by the outer rings 16, 17 of the adjacent bearing layers, for a complete squeezing of the tubing 4 to a maximum pressure level as needed from the pump.

Figure 5:
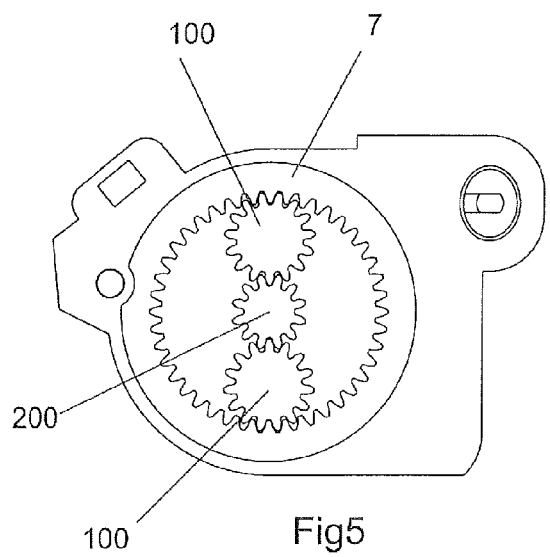
FIG. 5 shows a horizontal cross-section of the mechanism in a gear layer.

FIG. 5 shows the gear layer comprising an annulus outer gear ring 7 which specifies the position of the planet gears 100 in relation to the rotation of the central gear 200 which rotates through the coupling with a motor (not shown). The position of the central gear 200 is stable in the center of the outer gear 7. The nominal gear teeth distance for good operation and lower gearing friction is determined by the roller bearing layers shown in FIGS. 6 and 8 wherein the rollers 1, 2, 1 determine the exact respective teeth distance, which is otherwise achieved by a carrier in standard gear heads. In the rotary peristaltic mechanism 60 according to the present invention, the diameter of the central bushings 300 is dimensioned so that all tolerances of the bearings of the rollers and gears are not relevant. So, there is no axis friction which is otherwise caused by radial forces upon the bushing, and the diameter tolerance can be easily considered and adjusted by micro-molding as accurate moldings are available today.

More explicitly, FIG. 6 shows the lower roller bearing layer comprising the driving cylindrical central roller 2 and the planet rollers 1 which are in contact with the central roller 2 and the peripheral cylindrical outer ring 16 forming a 360° annulus, which assures as in all bearings that when squeezing the tubing 4 the counter-forces against the planet rollers 1 causes a force reaction at the bearing parts of all the three rollers 1, 2, 1 in line and, hence, are compensated and, hence, eliminated against each other. So, there is no friction in the central axis 210, 220, 230 since it is therefore not subject to any radial force. Further, there is no power consumption in contrast to the prior art elastic bearings having rotational friction. The reduced consumption has also the advantage of smaller pump dimensions and the need of a smaller motor and battery. The gear ratio and the diameter ratio of the rollers should be equal so as to have a rotation at the same angular speed for the cylindrical parts of the planet rollers 1 to roll over the outer rings 16, 17.

FIG. 7 shows as a third layer or stage the rotary peristaltic pump layer which does not comprise a body which is closed around 360° as in the gear and roller bearing layers, but is open at about 185°, wherein each planet roller 1 works as a pump rotary peristaltic roller squeezing the resilient tubing 4 against the outer wall of the cavity of the case 3 as shown in FIG. 4a. The radial depth of the cavity is smaller than the thickness of the tubing 4 in the uncompressed state so as to achieve the maximum infusion pressure of around 3 bar created by the pump action.

Figure 9:
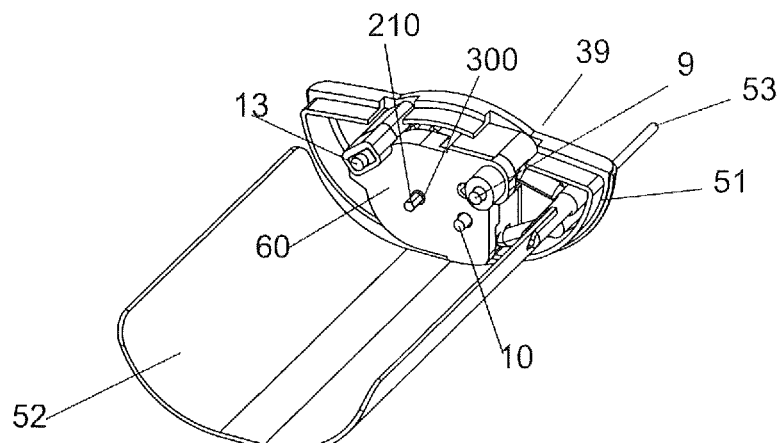
FIG. 9 shows the mechanism of FIGS. 1 to 8 mounted at an inner front side of a cassette.
Figure 14:
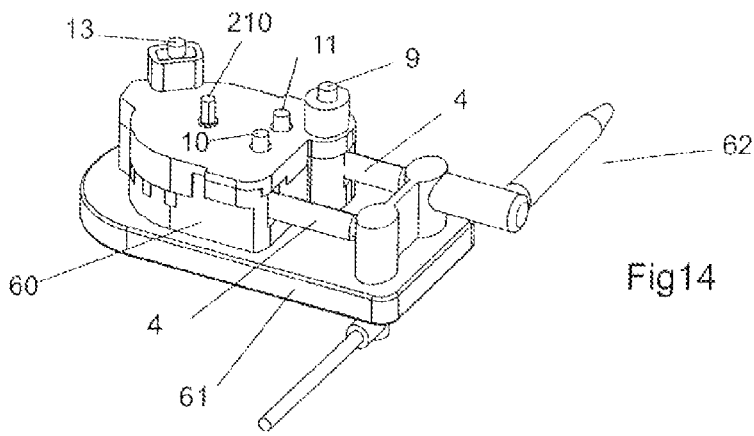
FIG. 14 shows a spike cassette with a filter and the mechanism of FIGS. 1 to 8.
Figure 18:
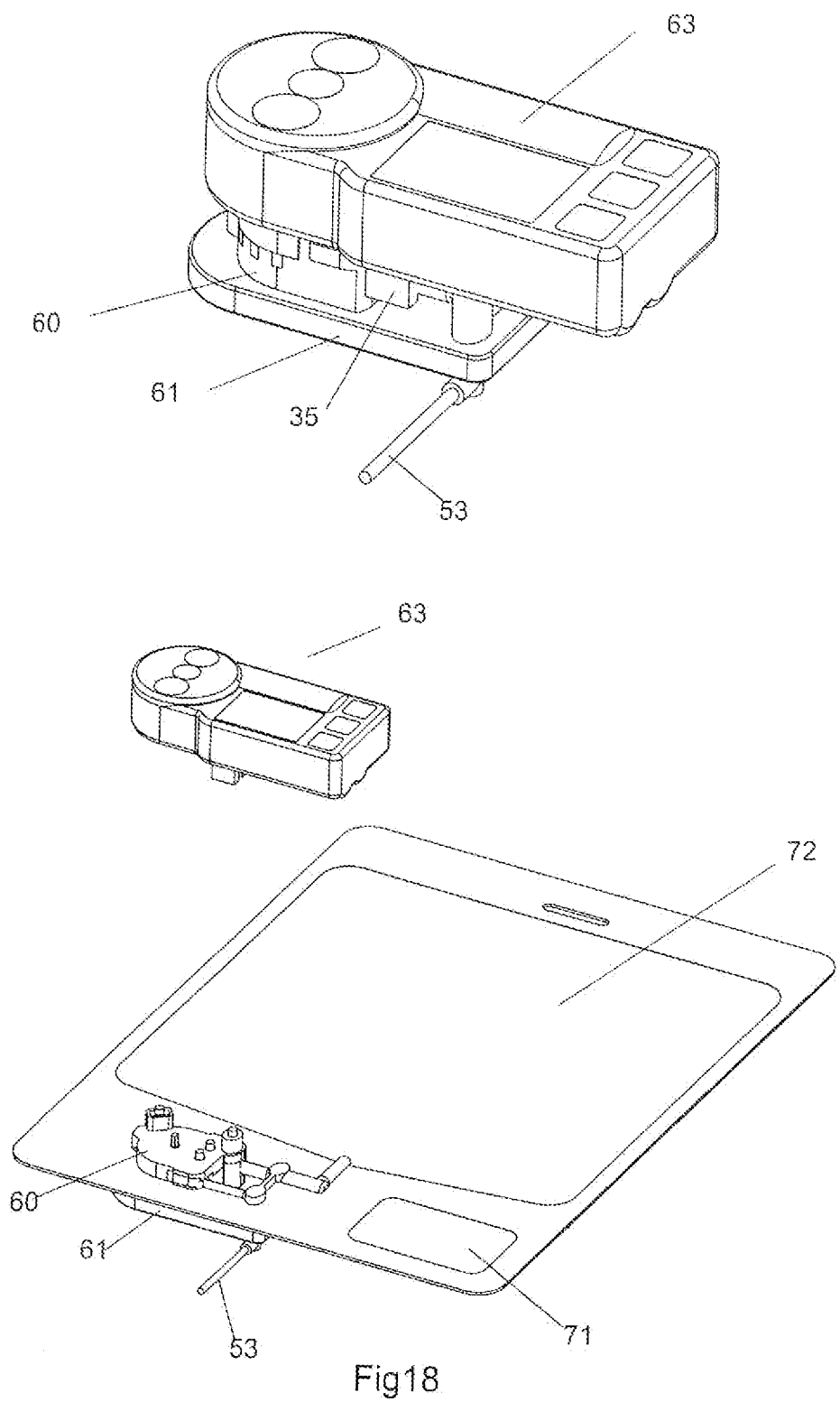
FIG. 18 shows the spike cassette of FIG. 14 directly mounted on a bag with the spike cassette infusion pump of FIGS. 15 and 16 separated therefrom.
Figure 19:
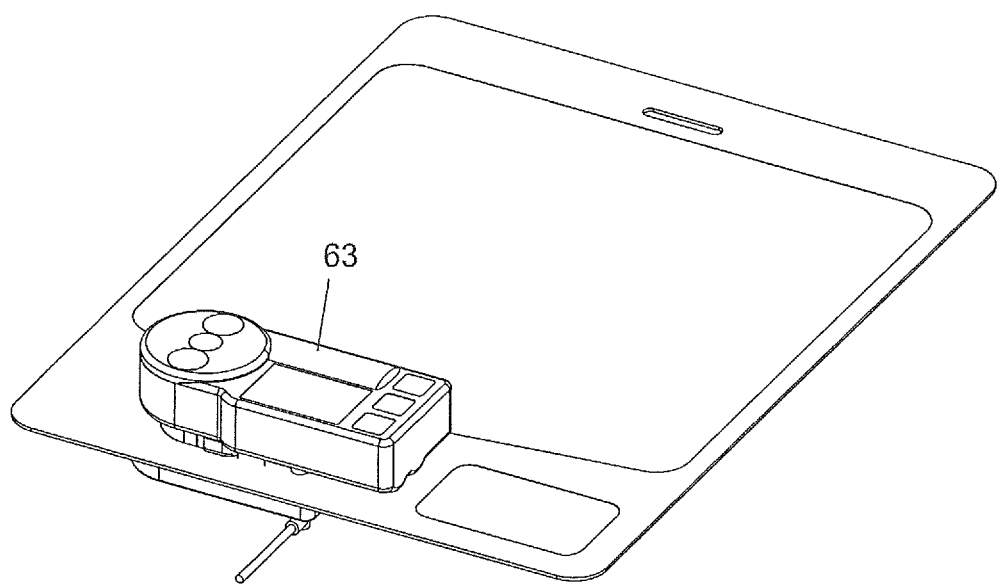
FIG. 19 shows the assembly of FIG. 17 mounted on the bag of FIG. 18.

The assembling of the rotary peristaltic mechanism 60 is easy and made for automatic and robotic assembly, i.e. by placing the three cylindrical rollers 1, 2, 1 with the gears 100, 200 aligned within the cavity of the lower part 14, then placing the outer gear 7, then placing the resilient tubing 4 with its fixation points 41, a stop 43 and a valve body 8, then placing two tubing relaxing parts 12, 13 which will be described below in detail, then placing a valve pin 9, then placing pressure actuators downstream (10) and in some models upstream (11), and finally placing the upper part 15 upon the lower part 14. Now, the rotary peristaltic mechanism 60 is ready to be fitted at the front side of a cassette-reservoir cover 51 as shown in FIG. 9 or on an air eliminating and anti-microbial filter amount 61 having a spike 62 as shown in FIG. 14, or by a direct connection with a bigger reservoir 72 as shown in FIG. 18, wherein these external mountings have upstream and downstream barb connections to the resilient tubing 4.

The rotary peristaltic mechanism 60 according to the present invention allows with a 20 mm diameter an infusion rate of 1000 ml/hr which is the highest required infusion pump rate for general infusions, while making also an extremely small size of mechanism for portable pumps.

In detail, the bent or round section of the resilient tubing 4 is an easy solution for medical infusion pumps, but it is not the best solution because the upper and lower horizontal walls of the tubing 4 along its round section are hard to be folded due to their tightness so that the one side part becomes flat against the other side part so that the initial cross-section shape of an "O" becomes an "8" shape and then an "I" shape resulting in blocking the flow. This phenomenon results in an unnecessary high energy consumption uninterruptedly or at least around the 180° working section of the peristaltic mechanism. According to the present invention, the section of the tubing 4 has a shape of a lens-type dual arc 42 with an acute angle or obtuse angle of its top and down tangents. This results in an easy and predictable folding without high energy since the upper and lower section of the tubing 4 is already angled, while it maintains its return into always the same open position after compression so as to achieve with accuracy the suction of always the same volume required for the infusion accuracy. Moreover, the resilient tubing 4 is not manufactured by extrusion like the tubings made of PVC or silicon as available on the market and used in pumps today, because such method may not guarantee the desired accuracy, since the control of the pulling-drawing stress of the tubing extrusion is not accurate due to a control tension roller oscillation with a spring which respectively creates alternate thick and thin tubing walls resulting in major differences of +/−15% (max. statistical error) although the standard deviation is 5%. The tubing 4 for the device according to the present invention is manufactured by a micro-molding injection process with an extreme accuracy. The material of the tubing 4 may be preferably an injection molded liquid silicon rubber (LSR) or TPE special for infusion tubing of adequate shore.

Figure 1:
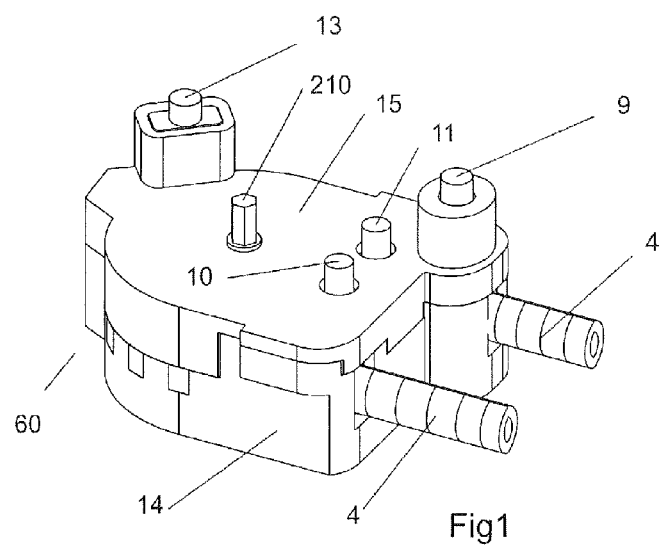
FIG. 1 shows a perspective view of a pump mechanism in an assembled state.
Figure 3:
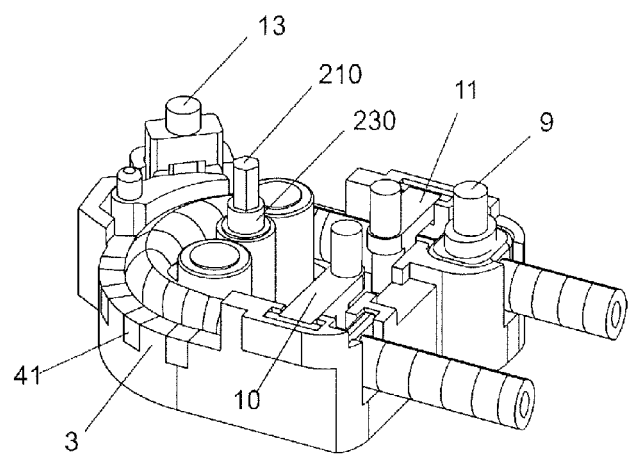
FIG. 3 shows a bottom sub-assembly of the mechanism of FIG. 1.
Figure 4:
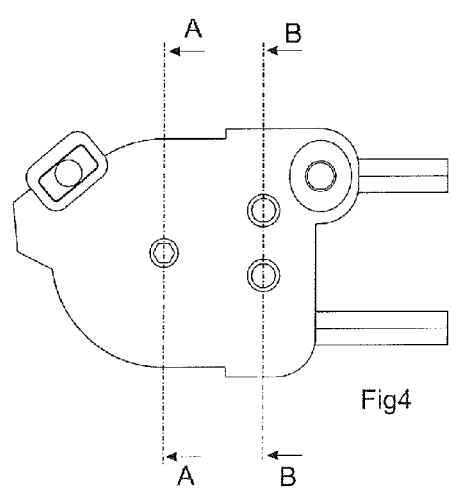
FIG. 4 shows a plan view of the mechanism of FIG. 4 along with a schematic indication of cross-sectional planes at lines A-A and B-B.
Figure 2:
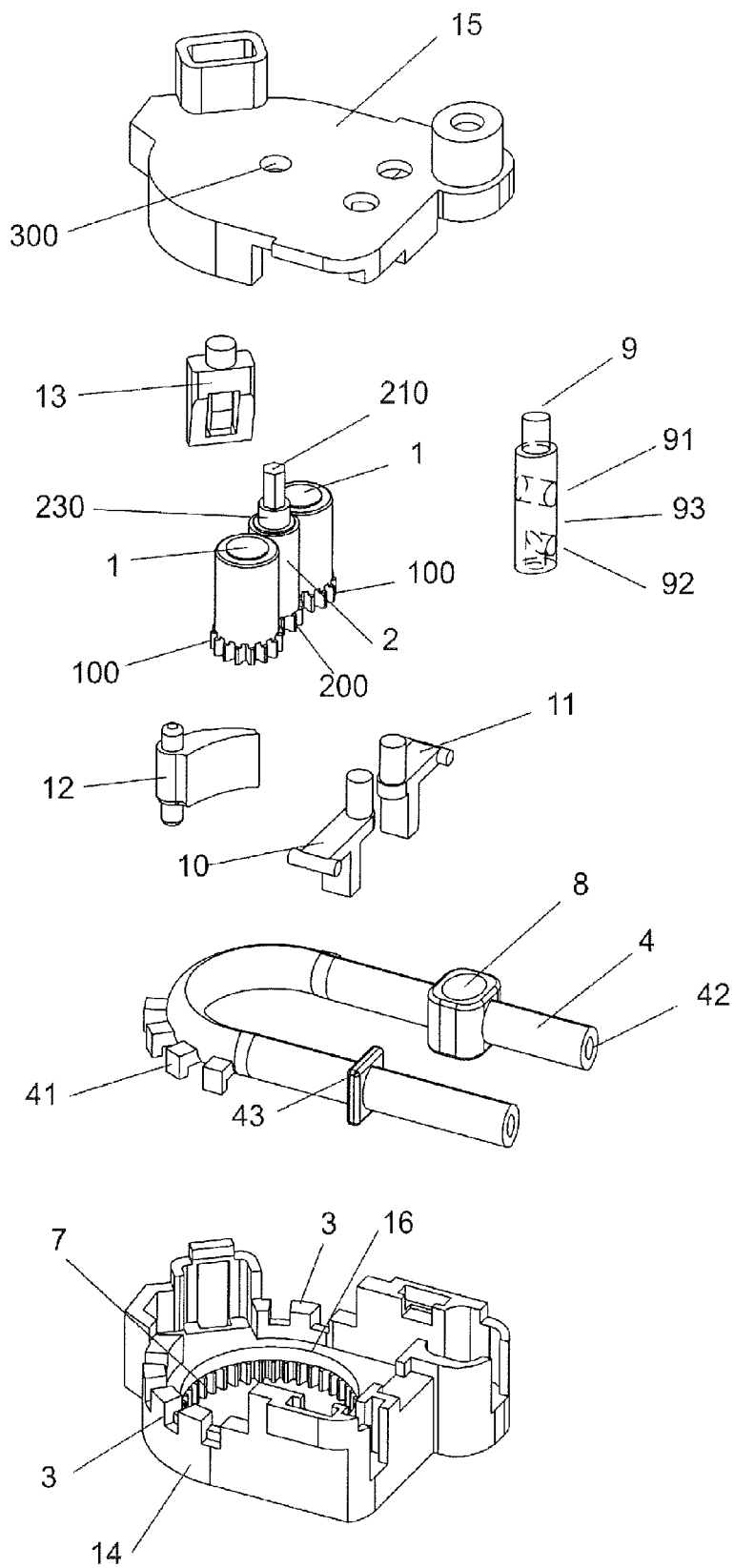
FIG. 2 shows an exploded view of the mechanism of FIG. 1.
Figure 4:
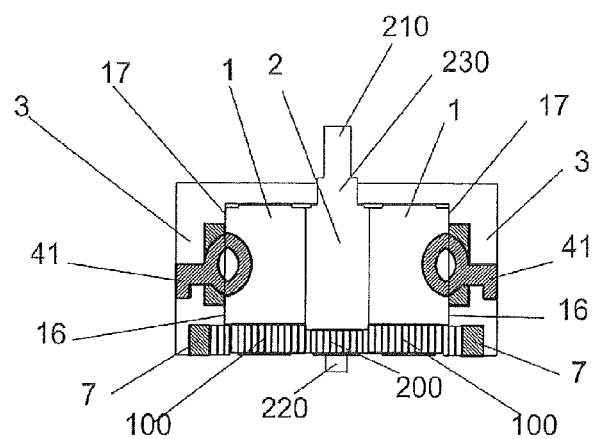
Figure 4:
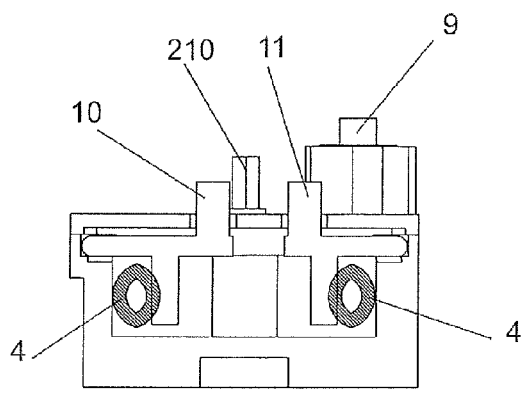

Moreover, according to the present invention, the resilient tubing 4 is fixed both tangentially and radially to the peripheral wall of the casing 3 by means of hooks 41 provided along the periphery of the tubing 4 and to be inserted into corresponding recesses provided in the peripheral wall of the casing 3 as it becomes clear in particular from the FIGS. 2 and 3. So it is not possible that the tubing 4 is pulled and extended during the rolling of the planet rollers 1; but the tubing 4 is fixed in a nominal and repeatable position during filling at the start of a peristaltic cyclus so as to have an enclosed liquid of exactly the same volume (due to unstressed dimensions of the tubing 4) as created by both planet rollers 1 at the same time in each rotation. Therefore, a better flow accuracy is achieved than that of linear peristaltic pumps. So, by using an injection molding for manufacturing the tubing 4, the following improvements are achieved: 1) dimensional accuracy leading to infusion accuracy, 2) fixing the tubing 4 with hooks 41 to the casing 3 so as to dramatically increase the accuracy which was not possible with a rotary peristaltic pump before, while the hooks 41 are distributed along the periphery so that they form somewhat like a star when put cyclically in place, and therefore the tubing 4 can be molded in a straight mold, and 3) the provision of a special lens-type (dual arc) shape of the walls of the tubing 4, resulting in a dramatically reduction of power consumption of the pump, while the walls are thick for high aspirating vacuum (measured at extreme −0.8 bar) needed for high rates infusion of viscous drugs like DUODOPA® and Immunoglobulin, and keeping high pressure in the tubing 4 even with not so good mechanism tolerances so as to work like a spring plate.

The accuracy is further improved with the use of forced-rolling rollers 1, 2, 1 as described above, so that they would have an active and not a passive (dragged) rotation. So, the stress on the tubing 4 is diminished without cost increase due to the overall design of plastic parts. In the device according to the present invention, the radius of compression of the tubing 4 can be adjusted so as to avoid pulling to either side, which increases the accuracy after a long use and diminishes power consumption. The overall accuracy with all the above improvements over the prior art essentially corresponds to that of syringe pumps, i.e. 1% to 2%. This allows the use in insulin and biological drug pumps and for other medicines requiring high infusion accuracy which is not feasible by means of prior art peristaltic pumps.

"Adjusted" radius of the rollers 1, 2 means that the radius of the portion of the rollers 1, 2 in the peristaltic pump layer must not be necessarily equal to the radius of the portions of the rollers 1, 2 in the roller bearing layers. Namely, a predominant gear bearing connected to a slave peristaltic pump load does not lead to the same perceived angular speed, wherein a roller at not-zero contact speed pushes or pulls the resilient tubing with friction on its surface.

The present invention makes use of such a function to pull or push the tubing 4 in a corrective way to either side at an experimental stage without fixing the tubing 4 on the walls of the case 3 so as to select and adjust an appropriate radius of the rollers 1, 2 in the peristaltic pump layer. Namely, apart from the known rolling friction, there is another component of friction which is not exactly known for the time being and changes its direction depending on the type and dimensions of the tubing and the rollers and sometimes becomes even zero (resulting in no pulling and no pushing of the tubing otherwise caused by the rollers). Such friction has to do with the non-linear transfer of the contact point in the periphery of the rollers with the tubing during the rolling, since the line of the contact between the roller and the tubing has a sinusoidal form, whereas the line of the transfer has a linear form. Therefore, the leveling of the tubing wall is made more violently in the first 45 rolling degrees of a roller, where there is less peripheral speed than nominal, and runs with smaller leveling in the next 45° and a greater peripheral speed. For each tubing, there is a stable equivalence of a corrected radius of a roller 1, 2 in the peristaltic pump layer and the radius of wall compression which does not help it to be pulled to either side because of the fixation to the walls of the casing 3.

The micro-molding technology allows the automatic production of the entire cassette or cartridge with high accuracies and small tolerances for the proper function of the gears and the rollers, for the bearing function and for the function of the tubing compression gap so that there is no need to provide a compression tolerance correction spring as in the prior art.

Means for leaving the resilient tubing 4 relaxed and unstressed, i.e. not compressed, during long storage and for easily passing the gas at sterilization with ethylene oxide are provided. In order to achieve this, according to a preferred embodiment a pivoting relaxing or releasing element 12 is provided which can be pivoted into a first or closed position for infusion wherein it forms a continuing part of the outer peripheral wall of the cavity which accommodates the tubing 4 so that the tubing 4 can be squeezed by the planet rollers 1, and into a second or open position wherein it is pivoted away from the tubing 4 so that in the region of the releasing element 12 the tubing 4 cannot be squeezed but is enabled to be relaxed and unstressed so that, in particular for sterilization purposes, fluids like liquids and/or air are allowed to freely pass through the tubing 4 with the pump not working and one planet roller 1 being placed in the region of the releasing element 12. However, if a planet roller 1 is placed at another portion of the tubing 4 different from the region of the releasing element 12, the tubing 4 will be squeezed and, hence, the infusion path will be closed irrespective of whether the releasing element 12 is in its first or second position, although the pump does not work. Further provided is a linearly movable cam 13 for pressing the releasing element 12 into its aforementioned first position. The cam 13 is adapted to be pressed by a pump body pin 58 so that the cam 13 is lowered and pushes the releasing element 12 into its first position for closing the outer peripheral wall of the cavity accommodating the tubing 4 so as to allow pumping action. So, during the use of the rotary peristaltic pumping mechanism 60, the releasing element 12 is placed in a nominal position with regard to the annulus for an appropriate compression of the tubing 4 by the planet rollers 1 so as to have a normal pumping function of the mechanism. In case the mechanism 60 is removed, no free flow occurs, as the releasing element 12 closes the flow since there is always a planet roller 1 squeezing the tubing 4 and the cam 13 is non-retractable.

Figure 23:
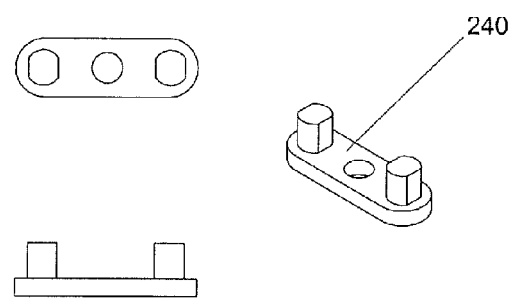
FIG. 23 shows different views of a narthex to be optionally provided.
Figure 24:
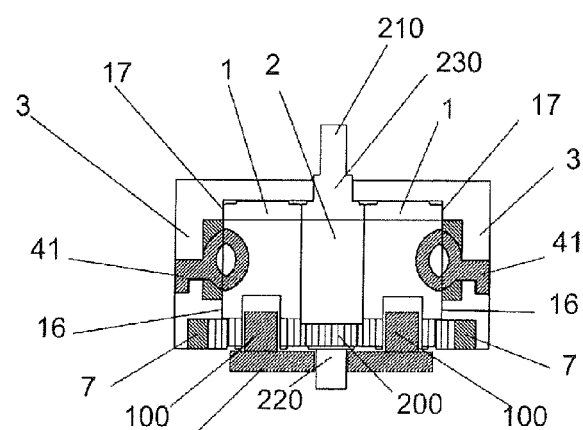
FIG. 24 shows the same view as FIG. 4 but with the narthex of FIG. 23 additionally arranged at the mechanism.

The present invention works fine without the need of any carrier as required in prior art rotary peristaltic pumps. Nevertheless, a risk management identifies that in case a tooth of any gear breaks or is missing for any reason, the alignment of the three cylindrical rollers 1, 2, 1 achieved by the gears 100, 200, 100 may be missed, a tooth jumping in a roller and a missing rotation step and in such a misalignment case free flow may occur, as the planet rollers 1 create an opening of more than 180° so that an occlusion path of the tubing 4 may be opened with at least one planet roller 1 being in the horseshoe-shaped infusion path of about 185°. For a remedy and without adding friction, a narthex 240 as shown in FIG. 23 can be preferably mounted at the mechanism 60 below the three rollers 1, 2, 1 under the gears 100, 200, 100 as shown in FIG. 24 or on the top wherein the narthex 240 is provided with pins to be axially inserted into all the three rollers 1, 2, 1 so as to ensure and guarantee the desired alignment in order to avoid any gear tooth breaking. The narthex 240 is rotating without any force subject onto it from the action and reaction forces since they compensate and, hence, eliminate each other as described above. The real exceptional case of missing and breaking a tooth is caused by forces which are oriented in a lateral direction. In order to make sure that radial forces do not occur, the pins are flat at their radial edges. This is why the element 240 is called a narthex rather than a carrier which normally drive the rollers resulting in the occurrence of force and friction in the prior art. If the narthex 240 is used, there is no need for providing a bushing 300 for the central gear 200 at the bottom of the lower part 14 of the housing of the mechanism 60, wherein a centering is achieved by the diametrically positioned planet rollers 1.

Figure 20:
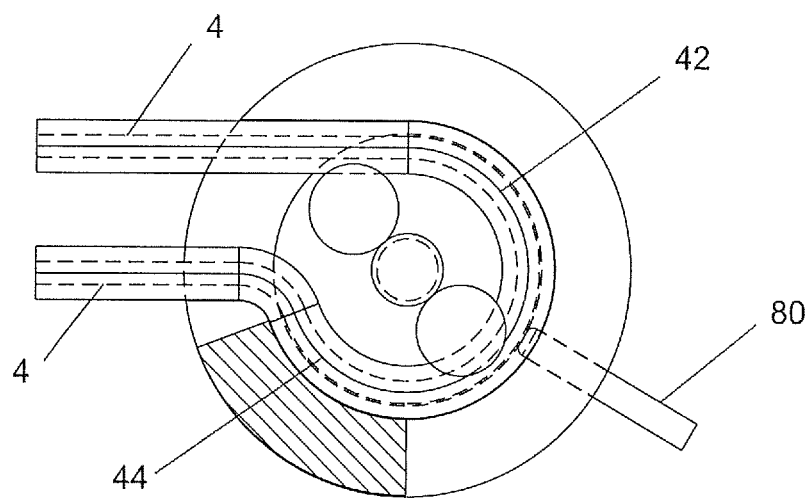
FIG. 20a to c schematically shows a horizontal cross-section of the mechanism of FIGS. 1 to 8 in the peristaltic pump layer according to a modification over the embodiment shown in FIG. 7 in different operational modes.
Figure 20:
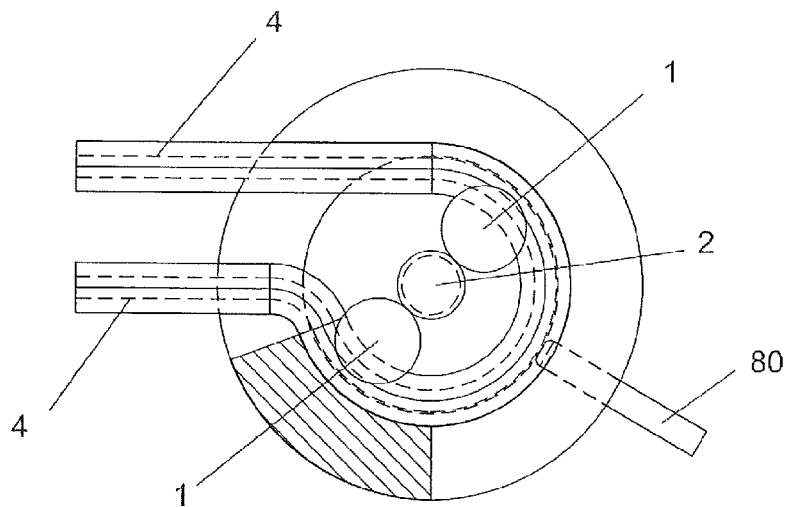
Figure 20:
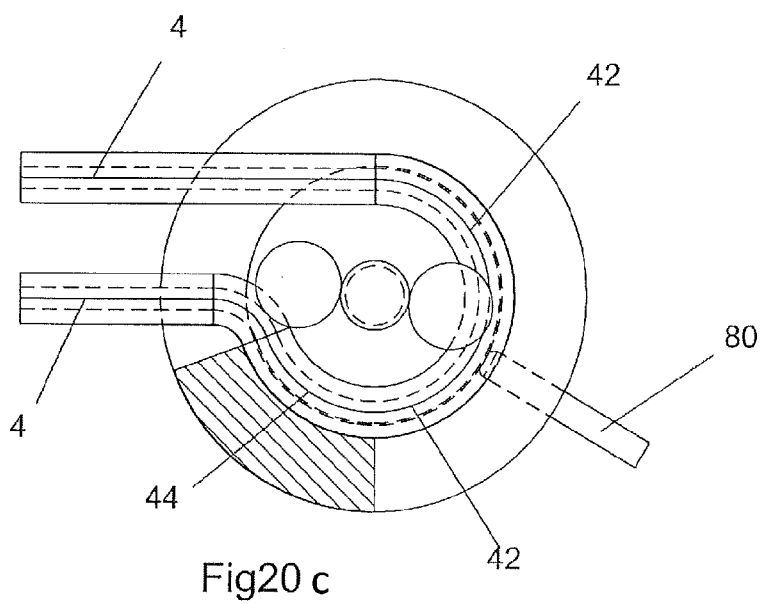
Figure 21:
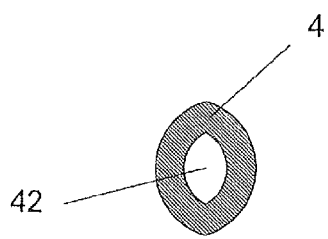
FIG. 21 shows a cross-section through a tubing with a normal inner opening cross-section (FIG. 21a) and a reduced inner opening cross-section (FIG. 21b)
Figure 21:
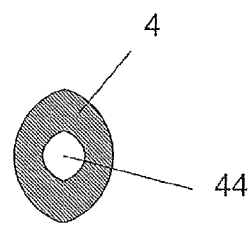

In FIGS. 20a to 20c another preferred embodiment of the mechanism 60 is shown which comprises an extension of the tubing 4 running circularly by some degrees beyond 180° downstream with a reduction of its diameter from point 42 to point 44 in that part. So, when the rollers 1 move a blocked-in liquid volume or move with a blocked-in liquid volume (180° after with both rollers being on the tubing 4) and with the enclosed volume being decreased due to the decrease of the internal diameter of the tubing 4, the pressure increases dramatically with the absence of air due to the fact that liquids are incompressible, whereas an increased pressure is gradually less when air in the blocked-in part is present or even increasing. Controlled by a pressure sensor 80 located at a selected position as shown in FIG. 20 are an upstream occlusion pressure when the sensor 80 senses the tubing 4 being open upstream (FIG. 20a), and a downstream occlusion pressure when the sensor senses the tubing 4 being open at the output (FIG. 20c) as well as air in line and any liquid leakage caused by a possible leak in the wall of the tubing 4, when the sensor senses a liquid pressurized by a reduced diameter part just before a downstream opening position (FIG. 20b). The pressure sensor is of the same type as the downstream or upstream pressure transmitting levers as described above.

An embodiment of the present invention may provide an extremely cheap and small pump without a sensor for the motor rotation but only with the pressure sensor sensing the fluctuation of pressure. The peristaltic pump layer may have more than one pumping stage for multi-pump arrangements with a flow rate in accordance with the resilient tubing size or infusion and aspiration if the upstream and downstream connections are reversed in one pump stage. This latter arrangement may be used as a dual infusion-aspiration pump as disclosed in US 2012/0289895.

The above described rotary peristaltic pumping mechanism 60 can be snap-fitted onto substrates of several preferred embodiments for different medical needs. In each case, resilient tubing and barb connections and an input and an output are placed on each substrate.

Figure 10:
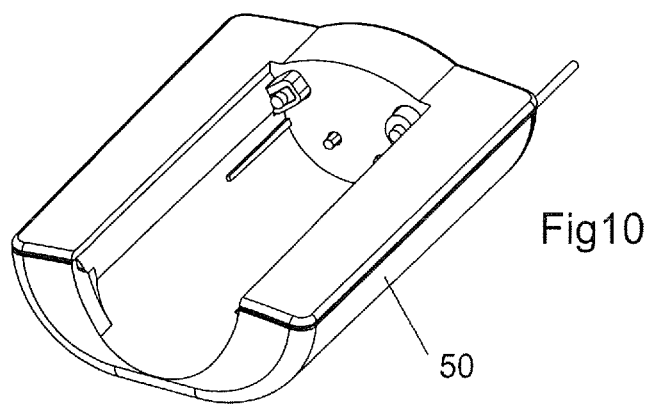
FIG. 10 shows the cassette of FIG. 9 with the mechanism of FIGS. 1 to 8 and a curved bag mounted thereon.

A semi-cylindrical cassette 50 made of a rather hard plastic as shown in FIG. 10 is provided for protecting a reservoir inside its cavity and to be used for pre-filled or compounded drugs or drugs to be filled in by a user.

If mounted on an air eliminating anti-microbial filter 61 with a spike 62, a pump-on-spike low-weight small size solution for spiked infusions is formed. If mounted on the same filter type but fitted permanently at the bottom of a reservoir with a direct connection to it, such an arrangement is useful for pre-filled larger volume drugs and is a solution with a better accuracy so as to replace balloon pumps.

The same automatic assembly machine can be used for assembling the mechanism 60 according to different embodiments (only with small differences, if needed at all) which comprise no upstream and downstream connections for the tubing 4 as provided at other devices.

The described embodiments of the present invention operate with the same infusion pump interaction which enables and triggers the desired functions as well as the sensors and the power, which include the coupling of a motor (not shown) by means of a protruding end of the central axis 210, the provision of a downstream pressure sensor (preferably embodied as a lever 10) and—in some configurations—an upstream pressure sensor (preferably embodied as a lever 11), pressing the linear cam 13 by the pump for engagement to trigger the blocking element 12 so that the mechanism 60 is ready for pumping action, and triggering the valve 9 so as to connect the tubing 4 to an infusion/sterilization passage 91 for sterilization and infusion.

The latter function, i.e. triggering the valve 9 so as to connect its infusion/sterilization passage 91 to the tubing 4, results in a connection of the hydraulically resilient tubing 4 to an input for connecting to a reservoir or spike. For using with a pre-filled bag, the valve 9 is moved relative to the body 8 which is provided in the tubing 4 and accommodates the valve 9, so that the valve 9 is arranged in a second (higher) position resulting in that a blocking portion 93 of the valve 9 closes the tubing 4, in particular after filling, so that there is no hydraulic connection between the components. If the valve 9 is moved to a third (highest) position, a filling passage 92 becomes effective to connect a filling port 39 to the bag 52, 72. However, in some configurations, the valve 9 may be always at the sterilization/infusion position with the infusion/sterilization passage 91 being effective for connection of the tubing 4 to the input for connection to the reservoir or spike. For sterilization ethylene oxide or gamma sterilization can be used. A protection case preferably made of vacuum formed type plastic can be placed over the described connecting parts 9, 10, 11, 13, 210. The valve can be embodied in a variety of concepts, like the provision of a hard plastic body 8 in the tubing 4 and a rubber pin 9 (being the 'real' valve), while the filling stage as provided by the filling passage 92 can be part of a filling machine at the site of a factory for drug combination or laboratory for compounding, so that the pin/valve 9 has only two stages as provided by the infusion/sterilization passage 91 and the blocking portion 93 for infusion/sterilization and blocking, respectively. According to a further alternative embodiment, even the valve can be provided on the reservoir itself and, hence, separately from the mechanism 60.

The filling of the reservoir by an end user may be done by means of a dedicated reverse cycle aspiration pump, or by means of the same infusion pump. By considering safety precautions in both such cases, a display should be provided to show the volume to be filled in so that a drug recipe can be realized easily by programming the aspirator with the drug recipe, in particular a list of volume, drug type and concentration to aspirate. For fast filling, a vacuum chamber leaving the filling port on its outer side can be used wherein a reservoir located inside the chamber is inflated by the vacuum so as to aspirate the drug from a dedicated needle or tubing or said filling port fixed thereon. A flow meter and a flow stop valve may be used for providing a professional recipe filling instrument. The described filling devices make the filling of a bag as easy as with a syringe pump but with no volume limitations (in particular more than 60 ml).

For use, according to a preferred embodiment of the present invention, the pump is provided on a cassette reservoir to replace syringe pumps for volumes up to 60 ml so as to realize a small handheld device for immunotherapy, Parkinson's disease therapy or a new generation of biological drugs which need extreme accuracy as achieved by the present invention.

Figure 13:
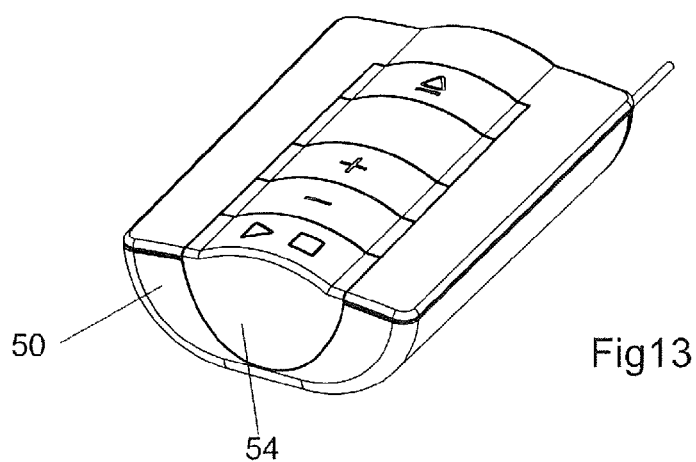
FIG. 13 shows the cassette of FIGS. 9 and 10 with the cassette infusion pump of FIGS. 11 and 12 mounted therein.

In this embodiment, a plate 51 defines a wall which is located at one end of the cassette 50 and is arranged essentially vertically with regard to the cassette 50 and provides the support of the mechanism 60, and the reservoir 52 is connected to the valve 9 so that it can be filled from the port 39 (cf. FIG. 9) by means of an automatic system in a pharmaceutical company and then pressed to lock it at a position wherein its blocking portion 93 becomes effective so that the pre-filled bag can be safely stored. The pre-filled bag is protected by a rigid or semi-rigid housing such as the described cassette 50. The controller 54 slides in the cavity of the cassette 50 as shown in FIG. 13 and is locked by a cam or pin not shown. By pressing a button 540 as shown in FIG. 11a for releasing the cam, the pump can be removed by sliding out again. When the controller 54 slides into the cassette 50, it pushes the valve 9 by means of a pin 55 shown in FIG. 11b to the infusion/sterilization position for opening the path of the tubing 4, further pushes the linear cam 13 to be engaged with the blocking element 12 and to move it into its first position for infusion wherein, however, a reverse free flow is not possible since there is always a planet roller 1 squeezing the tubing 4. A pressure sensor sealing membrane 56 shown in FIG. 11b makes contact with the lever 10 of the downstream pressure sensor, whereas an upstream pressure sensor comprising the lever 11 may be preferably not mounted as shown in FIG. 9 since it may not be needed in some cassette applications. A motor cobbler 57 is driving the central axis 210 which can be embodied as a hexagonal pin or any other type known in the art.

Figure 11:
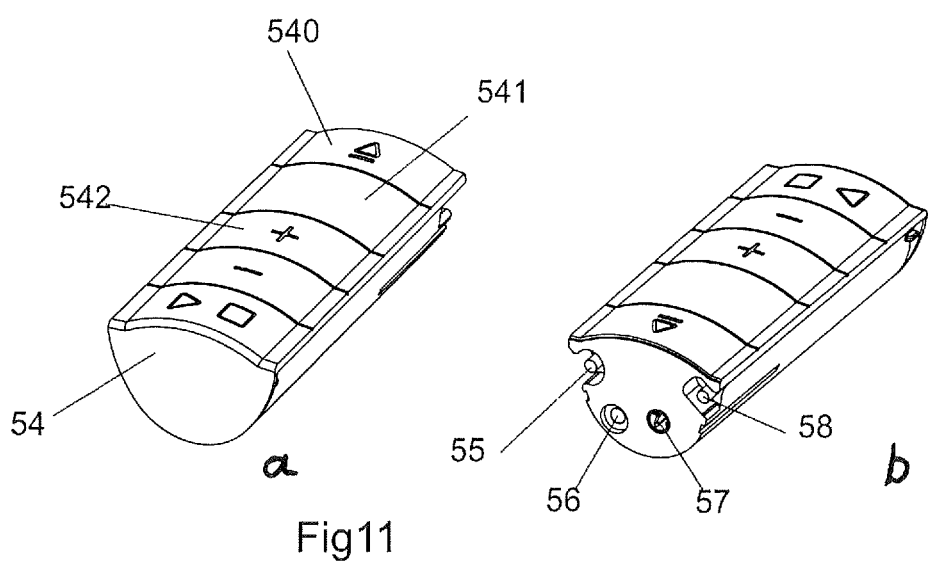
FIG. 11 shows a front side (FIG. 11a) and a back side (FIG. 11b) of a cassette infusion pump.
Figure 12:
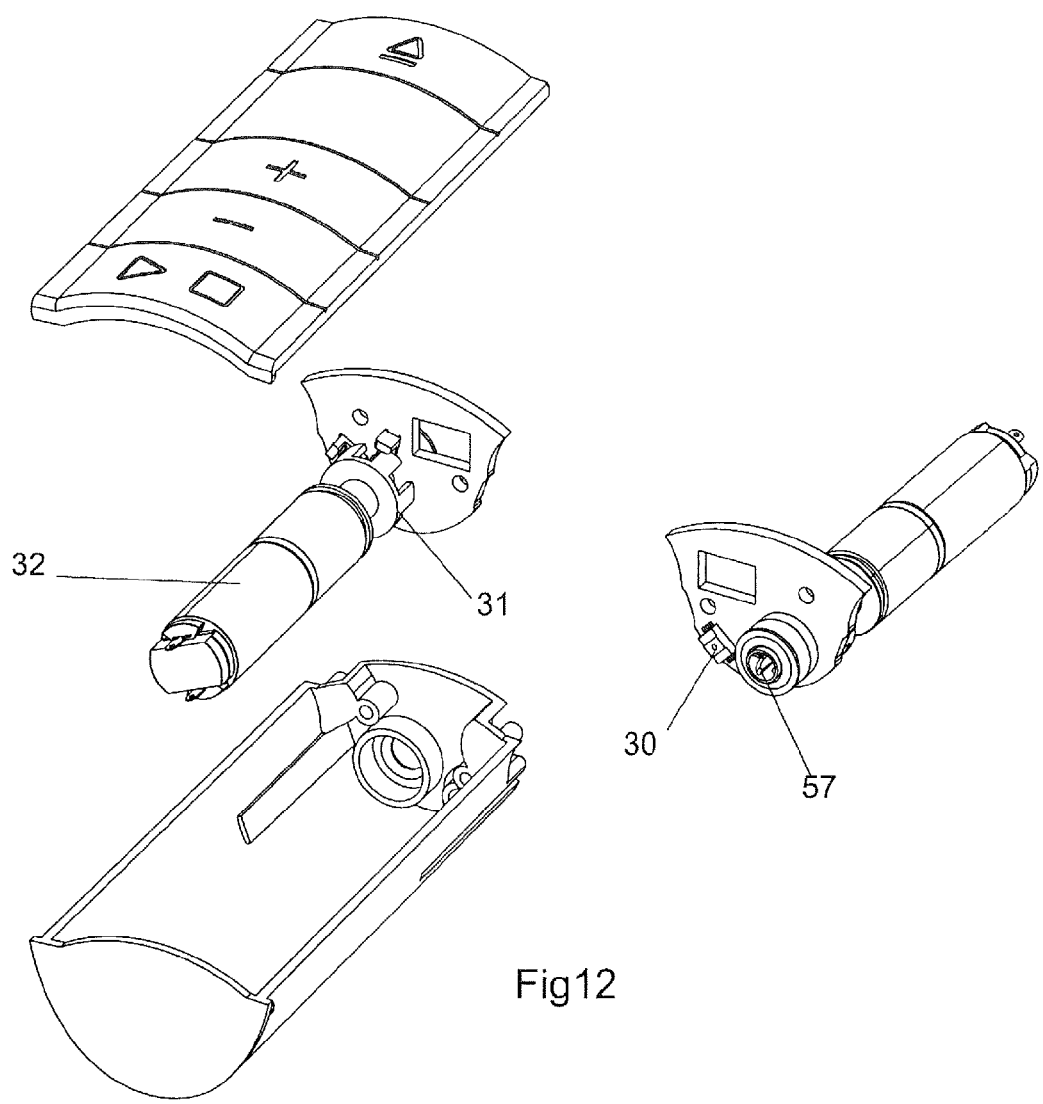
FIG. 12 shows an exploded view of the cassette infusion pump of FIG. 11.

The controller 54 comprises a display 541, keys 542, a motor 32, a positioning shutter 31 for, preferably optical, sensors, a pressure sensor 30, a battery, driving electronics etc. as it becomes clear from the FIGS. 11 and 12. The cassette 50 loaded with the controller 54 is shown in FIG. 13. The cassette 50 according to the present invention can be manufactured at low costs due to automatic production wherein no third party parts may be used for this purpose. Further, the cassette 50 according to the present invention has a high reliability since the pump has no wearing parts except for the motor, whereas all wearing peristaltic parts are provided in the mechanism 60. Moreover, the cassette may have no filter for subcutaneous infusions, but may have an air eliminating filter on the back of the plate 51 for IV infusions.

The material for the reservoir 52 can be PVC as a cheap solution, or a cyclic polyolefin (polypropylene) or multi-layer material for best long term stability in case of pre-filled drugs due to excellent humidity and gas barrier properties. Preferably, the reservoir 52 comprises an inner layer having micro-striations or texture to enable laminar microflow and prevent collapsing of its side walls as desired for mobile use.

Another preferred embodiment of the present invention may provide as a consumable device an entire miniaturized pump as a whole including a miniature cassette and a compounded insulin bag for diabetic patients wherein the motor is fixed over the cassette or cartridge and is preferably a flat piezoelectric/ultrasound motor like e.g. the "Flex motor model M10" with a movable pinion connected with a gear head over the drive axis of the mechanism. Such a motor is intended to be extremely cheap which is advantageous to realize the consumable pump device according to all the preferred embodiments.

Figure 15:
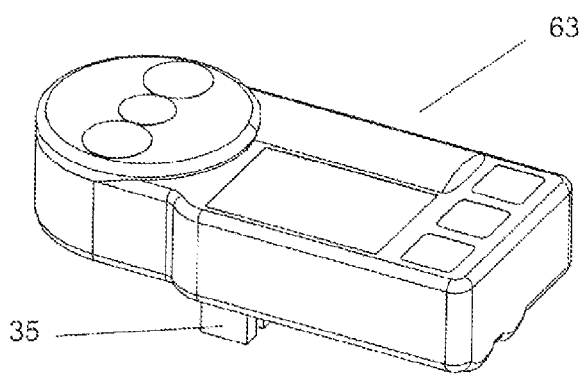
FIG. 15 shows a spike cassette infusion pump.

A new concept of the consumable pump device including a filter for parenteral nutrition with already prepared nutrition bags and other higher volume therapies as well as for the general infusion market where low cost is prerequisite contains an anti-microbial filter with air elimination 61 (as known in the art) as a substrate for the mechanism 60 as shown in FIG. 14. For such an application, an upstream pressure 11 including a lever is mounted which is adapted to detect when the bag is empty (collapsed), an air-in-line (AIL) ultrasound detector 35 is mounted on the spike controller 63 including the resilient tubing 4 which due to its lens-type form facilitates an easy press-in snap fit insertion. In this embodiment, the same actuators 9, 13 are pressed by fitting the pump wherein the two pressure sensors, a motor and the AIL detector 35 are provided as shown in FIG. 15.

The device has such a low weight that it can be hanged on the spike 62 wherein a friction force for retaining the pump occurs. However, hanging clips (not shown) can be used, too. This results in a reduction of the occupied space in ICUs and hospital recovering rooms and a reduction of medication errors as the pump shows just on the drug bag what is the infusion protocol, i.e. there is no confusion of which infusion line goes to which pump where many pumps are infusing the same patient. The valve 9 has a button behind the filter with a press to clamp action for bringing the valve 9 into its blocking position with the blocking portion 93 blocking any flow connection, whereas the clamp opens the flow connection when the valve 9 is moved into its infusion/sterilization position with the infusion/sterilization passage 91 connecting the tubing 4 to an external bag when the pump is brought into a press fit onto the consumable pump device. Snap-fitting and releasing of the controller 54 is done by actuating the button 540 or a key. The controller design extending along the bag results in an overall small size which is helpful in case both the pump and the bag are placed in a rucksack (parenteral nutrition) or a banana bag (local analgesia). The direct connection of the pump mechanism to a spike according to the present invention avoids upstream occlusions which annoy nurses with alarms quite often.

The controller comprises a small display which preferably comprises organic polymer and has an ultra-low weight and power consumption. Further, the pump is connected (wired or wireless) in a network system which spreads the information to several other system visualizing and programming devices which are also adapted to recognize RFID/NFC labels 71 as described in US 2012/0016295A1.

Figure 16:
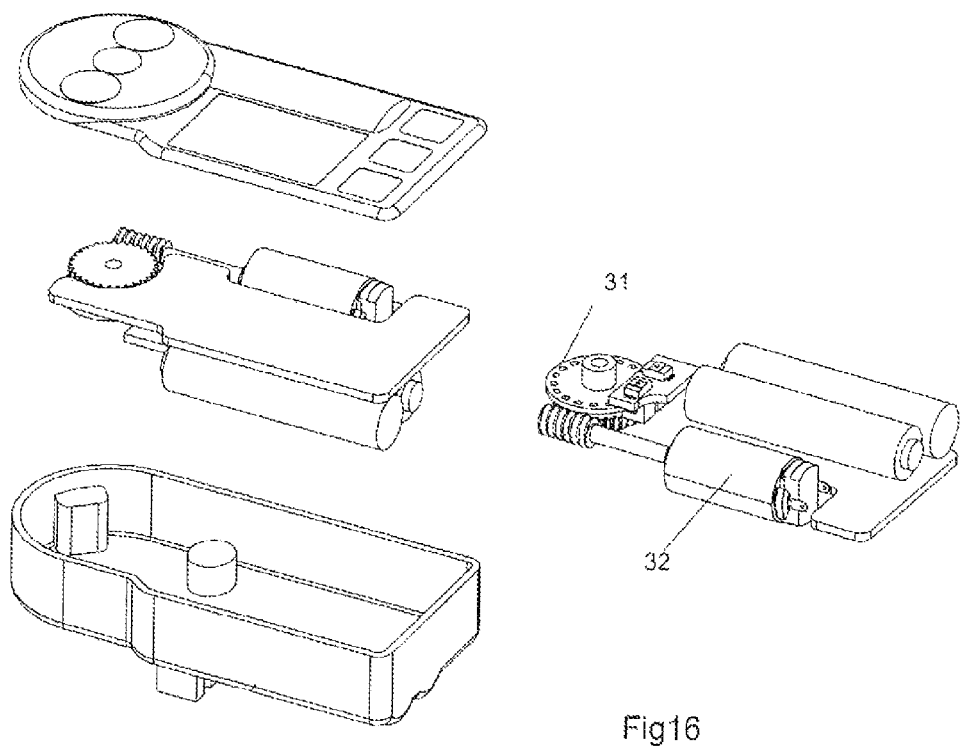
FIG. 16 shows an exploded view of the spike cassette infusion pump of FIG. 15.

This pump system can be manufactured by an automatic production by using no third party parts resulting in extremely low costs, which applies to the motor 32 in the controller 63 (FIG. 12) as well. Other parts as shown in FIG. 16 are an optical positioning disc 31 and, preferably rechargeable, batteries. As a pump display, tablet PCs can be used for managing a plurality of pumps, transferring and recharging power and processing data, to be hanged at the same pole along with their respective drug bags.

A new concept of the consumable pump-on-bag device for a compounded or empty bag provides for a mechanism 60 which is fixed, preferably press-fit clamped, to a bag as shown in FIG. 18 with the filter 61 arranged below and the upper part 15 of the mechanism 60 on the top wherein the level of the tubing is essentially at the level of the bag material. The input is in direct connection with the bag so as to avoid upstream occlusions, and a downstream tubing 53 (FIG. 18) is provided below as an output, while the connector type depends upon the application, i.e. Luer-lock male for standard infusions, female for internal nutrition, special type for epidural etc.

The material of the reservoir 52 can be PVC as a cheap solution, or cyclic polyolefin (polypropylene) or multi-layer material for best long term stability of pre-filled drugs due to excellent humidity and gas barrier properties. This mechanism has the valve 9 in a ready to fill position with the filling passage 92 connecting the inlet of the tubing 4 to an external filling port coupled to an external reservoir. Further, a press-to-clamp pin from behind (not shown) can clamp the valve 9 after filling in the blocking position with the blocking portion 93 blocking the flow connection. When plugged in, the controller 54 places the valve 9 in its infusion/sterilization position with the infusion/sterilization passage 91 connecting an external bag to the inlet of the tubing 4. In case the bag is pre-filled with a specific drug by a pharmaceutical company, a label 71 can be provided close to the mechanism 60 which label contains an RFID/NFC (near field communicator) wireless data chip so that the controller 63 can automatically recognize the drug name, volume, concentration, diluter and eventually the protocol and patient name (in particular in a reprogramming case) stored in the chip; these data can be sent e.g. to a distributed pump system according to US 2012/0016295A1 disclosing a patient centric programming system. The RFID chip can be programmed at the near end of infusion so that the pump retains its identification number and reuse of the same cassette is not permitted by the pump software after first use. The pump can also be provided with a long tubing 53 at the output for therapies like parenteral nutrition, with no contamination at the pump outlet (no use of a spike).

The bag can be used as a balloon pump replacement in chemotherapy if the pump is used for one time or few times, i.e. by using a toy motor or a new type of a cheap stepper motor ("Portescap") for the controller 63 and for a number of mechanical bags. The advantages are extreme accuracy, ease of filling with the vacuum filler or aspiration pump, predictable results and a therapy filling up through the applicant's distributed pump system. The controller 63 is very small so that every nurse can have one or more such pumps in the pocket and place it on bags everywhere in the hospital or at home.

The invention claimed is:
1. An infusion pump device, comprising:
  a housing which is divided into at least three operating layers positioned one above the other, wherein
  a first operating layer includes an epicyclic gear means comprising a rotatable central gear, a stationary outer ring gear surrounding the central gear, and movable planet gears which are arranged between the central gear and the ring gear and in movable engagement with both the central gear and the ring gear,
  a second operating layer includes a roller bearing means comprising a stationary outer ring and a movable inner roller arrangement, wherein the inner roller arrangement comprises a rotatable central roller and movable planet rollers which are arranged between the central roller and the outer ring and in movable frictional direct engagement with both the central roller and the outer ring and the inner roller arrangement is in movable arrangement with the outer ring and coupled with the epicyclic gear means so as to provide a rotational bearing for the central and planet gears, and
  a third operating layer includes a rotary peristaltic pump means comprising a stationary flexible, preferably resilient, tubing which includes a bent portion having an essentially part-cycle form, and a rotor which is provided with engagement elements for locally engaging the bent portion of the flexible tubing so as to squeeze it during rotation for a pump action, wherein the rotor is coupled with the central gear of the epicyclic gear means so that a torque is transferred from the central gear to the rotor.

2. The device according to claim 1, wherein the rotor is non-rotatably coupled in coaxial arrangement with the central gear of the epicyclic gear means.

3. The device according to claim 1, wherein the inner roller arrangement of the roller bearing means is non-rotatably coupled with at least the central gear of the epicyclic gear means.

4. The device according to claim 1, wherein the central gear of the epicyclic gear means is non-rotatably coupled in coaxial arrangement with the central roller of the roller bearing means.

5. The device according to claim 1, wherein at least one of the planet gears of the epicyclic gear means is non-rotatably coupled in coaxial arrangement with one of the planet rollers of the roller bearing means.

6. The device according to claim 1, wherein the roller bearing means comprises two planet rollers which are arranged essentially diametrically opposite to the rotary axis of the central roller.

7. The device according to claim 1, wherein the epicyclic gear means comprises two planet gears which are arranged essentially diametrically opposite to the rotary axis of the central gear.

8. The device according to claim 1, wherein the engagement elements of the rotor of the rotary peristaltic pump means are provided as engagement rollers at least one of which is non-rotatably coupled in coaxial arrangement with one of the planet gears of the epicyclic gear means.

9. The device according to claim 8, wherein the rotor of the rotary peristaltic pump means comprises a central roller which is in frictional engagement with the engagement rollers and is non-rotatably coupled in coaxial arrangement with the central gear of the epicyclic gear means.

10. The device according to claim 9, wherein the gear ratio between the planet gears and the central gear of the epicyclic gear means corresponds to the ratio between the diameter of the engagement rollers and the diameter of the central roller of the rotor of the rotary peristaltic pump means.

11. The device according to claim 9, wherein the central gear of the epicyclic gear means, the central roller of the roller bearing means and the central roller of the rotor of the rotary peristaltic pump means are integrally formed as one piece, or wherein a planet gear of the epicyclic gear means, a planet roller of the roller bearing means and an engagement roller of the rotor of the rotary peristaltic pump means are integrally formed as one piece.

12. The device according to claim 8, wherein the rotor of the rotary peristaltic pump means comprises two engagement rollers which are arranged essentially diametrically opposite to the rotary axis of the rotor.

13. The device according to claim 1, further comprising fixing means for fixing the tubing to the housing so as to prevent radial and peripheral sliding of the tubing relative to the housing.

14. The device according to claim 1, further comprising relaxing means adapted to relax the tubing and to restore its nominal operational diameter, with one engaging element positioned against it or in case the rotary peristaltic pump means is not in an operational mode.

15. The device according to claim 1, wherein the rotary peristaltic pump means comprises an inlet and an outlet, the tubing extends from the inlet to the outlet, and at the inlet provided is a 3-way valve including a passage adapted to connect an external bag to the inlet, a blocking portion adapted to close the inlet, and a filling passage adapted to connect the inlet to an external filling port coupled to an external reservoir.

16. The device according to claim 15, further comprising a controller, which includes a first pin, a second pin, a cobbler and at least a pressure sensor element, wherein the first pin is adapted to open the valve for infusion so as to connect an external bag to the inlet by the passage when the controller is arranged at a cartridge, the second pin is adapted to control the relaxing means so that the tubing cannot be relaxed when the controller is arranged at the cartridge, the cobbler is adapted to engage a motor so as to drive the central gear of the epicyclic gear means when the controller is arranged at the cartridge, and the at least one pressure sensor element is adapted to engage with at least a pressure sensor for detecting the pressure in the tubing when the controller is arranged at the cartridge.

17. The device according to claim 1, further comprising a port for connecting to an external bag, and a tag, preferably a wireless tag like an RFID tag, in particular for identification of the content of the external bag and of the therapy.

18. The device according to claim 17, further comprising an inlet adapted for a direct connection to a bag or reservoir.

19. The device according to claim 1, further comprising a filter, preferably an air eliminating filter, as a substrate for supporting the housing.

20. The device according to claim 19, further comprising an inlet spike.

21. The device according to claim 1, wherein the tubing comprises means for coupling with an air-in-line detection means.

22. The device according claim 1, further comprising a cassette for accommodation of a liquid reservoir.

23. The device according to claim 22, wherein the cassette has essentially the shape of a half cylinder.

24. The device according to claim 22, wherein the cassette comprises a wall which is adapted to mount the housing and preferably extends essentially vertically.

25. The device according to claim 1, further comprising a narthex which is adapted to provide a rotational bearing for the central gear of the epicyclic gear means.

* * * * *